United States Patent
Yeung et al.

(10) Patent No.: US 11,905,237 B2
(45) Date of Patent: Feb. 20, 2024

(54) ACCESS TO CHIRAL BISPHENOL (BPOL) LIGANDS THROUGH DESYMMETRIZING ASYMMETRIC ORTHO-SELECTIVE MONO-HALOGENATION

(71) Applicant: The Chinese University of Hong Kong, Hong Kong (CN)

(72) Inventors: Ying-Yeung Yeung, Hong Kong (CN); Xiaodong Xiong, Nanchang (CN); Tianyu Zheng, Hong Kong (CN); Xinyan Wang, Guangdong (CN); Ying-Lung Steve Tse, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 125 days.

(21) Appl. No.: 17/212,605

(22) Filed: Mar. 25, 2021

(65) Prior Publication Data

US 2021/0300853 A1 Sep. 30, 2021

Related U.S. Application Data

(60) Provisional application No. 63/001,929, filed on Mar. 30, 2020.

(51) Int. Cl.
| | | |
|---|---|---|
| *C07C 37/62* | (2006.01) | |
| *B01J 31/24* | (2006.01) | |
| *C07C 37/18* | (2006.01) | |
| *C07F 9/24* | (2006.01) | |
| *C07C 39/367* | (2006.01) | |

(52) U.S. Cl.
CPC ........... *C07C 37/62* (2013.01); *B01J 31/2404* (2013.01); *C07C 37/18* (2013.01); *C07C 39/367* (2013.01); *C07F 9/2404* (2013.01); *C07B 2200/09* (2013.01)

(58) Field of Classification Search
None
See application file for complete search history.

(56) References Cited

PUBLICATIONS

Hurtley (Hurtley, A. E. et al. "Desymmetrization of Diarylmethylamido Bis(phenols) through Peptide-Catalyzed Bromination: Enantiodivergence as a Consequence of a 2 amu Alteration at an Achiral Residue within the Catalyst" J. Am. Chem. Soc. 2006, 128, 6276-6277) (Year: 2006).*
Chen (Chen, A-J. et al. "Highly Efficient and Regioselective Halogenation over Well Dispersed Rhenium-Promoted Mesoporous Zirconia" ACS Catal. 2011, 1, 786-793) (Year: 2011).*
Cho (Cho, J. K. et al. "Captured and Cross-Linked Palladium Nanoparticles" J. Am. Chem. Soc. 2006, 128, 6276-6277) (Year: 2006).*
Farina, V. et al., "Asymmetric Synthesis of Active Pharmaceutical Ingredients", *Chem. Rev.*, 2006, 106:2734-2793, American Chemical Society.
Trost, B.M., "Asymmetric catalysis: An enabling science", *PNAS*, Apr. 13, 2004, 101(15):5348-5355, The National Academy of Sciences of the USA.
List, B et al., "The Organic Approach to Asymmetric Catalysis", *Science*, Sep. 15, 2006, 313(5793): 1584-1586, American Association for the Advancement of Science.
MacMillan, D.W.C., "The advent and development of organocatalysis", *Nature*, Sep. 18, 2008, 455(18):304-308, Macmillan Publishers Limited.
Yoon, T.P. et al., "Privileged Chiral Catalysts", *Science*, Mar. 14, 2003, 299(5613):1691-1693.
Chen, Y. et al., "Modified BINOL Ligands in Asymmetric Catalysis", *Chem. Rev.*, 2003, 103(8):3155-3211, American Chemical Society.
Bringmann, G. et al., "Atroposelective Synthesis of Axially Chiral Biaryl Compounds", *Angewandte Chemie Int. Ed.*, 2005, 44:5384-5427, Wiley-VCH Verlag Gmbh & Co. KGaA, Weinheim.
Brunel, J.M., "BINOL: A Versatile Chiral Reagent", *Chem. Rev.*, 2005, 105(3):857-897, American Chemical Society.
Akiyama, T., "Stronger Brønsted Acids", *Chem. Rev.*, 2007, 107(12):5744-5758, American Chemical Society.
Terada, M., "Binaphthol-derived phosphoric acid as a versatile catalyst for enantioselective carbon-carbon bond forming reactions", *Chem. Commun.*, 2008, pp. 4097-4112, The Royal Society of Chemistry.
Rueping M. et al., "Chiral Brønsted acids in enantioselective carbonyl activations—activation modes and applications", *Chem. Soc. Rev.*, 2011, 40:4539-4549, The Royal Society of Chemistry.
Čorić, I. et al., "Asymmetric spiroacetalization catalysed by confined Brønsted acids", *Nature*, Mar. 15, 2012, 483:315-319, Macmillan Publishers Limited.
Sun, Z. et al., "Chiral Phosphoric Acid-Catalyzed Enantioselective and Diastereoselective Spiroketalizations", *Journal of the American Chemical Society*, 2012, 134:8074-8077, American Chemical Society.
Wang, Y.B. et al., "Construction of Axially Chiral Compounds via Asymmetric Organocatalysis", *Acc. Chem. Res.*, 2018, 51:534-547, American Chemical Society.
Seebach, D. et al., "TADDOLs, Their Derivatives, and TADDOL Analogues: Versatile Chiral Auxiliaries", *Angew. Chem. Int. Ed.*, 2001, 40:92-138, Wiley-VCH Verlag GmbH, D-69451 Weinheim.
Pellissier, H., "Use of TADDOLs and their derivatives in asymmetric synthesis", *Tetrahedron*, 2008, 64:10279-10317, Elsevier Ltd.

(Continued)

*Primary Examiner* — Medhanit W Bahta
(74) *Attorney, Agent, or Firm* — SALIWANCHIK, LLOYD & EISENSCHENK

(57) ABSTRACT

The subject invention pertains to a method of halogenating phenols, yielding a range of halogenated phenols with enantiomeric ratio of up to 99.5:0.5. In certain embodiments, the subject invention pertains to a method of asymmetric halogenation of bisphenol, yielding a range of chiral bisphenol ligands. The novel chiral bisphenols are potent privileged catalyst cores that can be applied to the preparation of ligands for various catalytic asymmetric reactions. The catalyst library can easily be accessed because late-stage modification of the scaffold can readily be executed through cross-coupling of the halogen handles on the bisphenols.

15 Claims, 7 Drawing Sheets

(56) References Cited

PUBLICATIONS

Fu, Y. et al., "Novel monodentate spiro phosphorus ligands for rhodium-catalyzed hydrogenation reactions", *Chem. Commun.*, 2002, pp. 480-481, The Royal Society of Chemistry.

Xie, J.H. et al., "Chiral Diphosphine and Monodentate Phosphorus Ligands on a Spiro Scaffold for Transition-Metal-Catalyzed Asymmetric Reactions", *Accounts of Chemical Research*, May 2008, 41(5):581-593, American Chemical Society.

Duan, H.F. et al., "Enantioselective Rhodium-Catalyzed Addition of Arylboronic Acids to α-Ketoesters", *Angewandte Chemie Int. Ed.*, 2008, 47:4351-4353, Wiley-VCH Verlag Gmbh & Co., KGaA, Weinheim.

Hou, G.H. et al., "Iridium-Catalyzed Asymmetric Hydrogenation of Cyclic Enamines", *Journal of American Chemical Society*, 2009, 131(4):1366-1367, American Chemical Society.

Chung, Y.K. et al., "Phosphine-Catalyzed Enantioselective Synthesis of Oxygen Heterocycles", *Angewandte Chemie Int. Ed.*, 2009, 48:2225-2227, Wiley-VCH Verlag Gmbh & Co., KGaA, Weinheim.

Ding, K. et al., "Spiro Skeletons: A Class of Privileged Structure for Chiral Ligand Design", *Chem. Asian J.*, 2009, 4:32-41, Wiley-VCH Verlag Gmbh & Co., KGaA, Weinheim.

Dong, K. et al., "Rh(I)-Catalyzed Enantioselective Hydrogenation of α-Substituted Ethenylphosphonic Acids", *Journal of American Chemical Society*, 2012, 134:12474-12477, American Chemical Society.

Wu, C. et al., "Asymmetric Conjugate Addition of Organoboron Reagents to Common Enones Using Copper Catalysts", *Journal of American Chemical Society*, 2016, 138:742-745, American Chemical Society.

Ćorić, I. et al., "Kinetic Resolution of Homoaldols via Catalytic Asymmetric Transacetalization", *Journal of American Chemical Society*, 2010, 132:17370-17373, American Chemical Society.

Xu, F. et al., "SPINOL-Derived Phosphoric Acids: Synthesis and Application in Enantioselective Friedel—Crafts Reaction of Indoles with Imines", *J. Org. Chem.*, 2010, 75:8677-8680, American Chemical Society.

Xu, B. et al., "Asymmetric N-H Insertion Reaction Cooperatively Catalyzed by Rhodium and Chiral Spiro Phosphoric Acids", *Angewandte Chemie Int. Ed.*, 2011, 50:11483-11486, Wiley-VCH Verlag GmbH & Co., KGaA, Weinheim.

Wang, G.P. et al., "Enantioselective Nazarov cyclization of indole enones cooperatively catalyzed by Lewis acids and chiral Brønsted acids", *Chemical Science*, 2017, 8:7197-7202, The Royal Society of Chemistry.

Birman, V.B. et al., "1,1'-Spirobiindane-7,7'-diol: a novel, $C_2$-symmetric chiral ligand", *Tetrahedron: Asymmetry*, 1999, 10:125-131, Elsevier Science Ltd.

Zhang, J.H. et al., "Highly efficient and practical resolution of 1,1'-spirobiindane-7,7'-diol by inclusion crystallization with N-benzylcinchonidinium chloride", *Tetrahedron: Asymmetry*, 2002, 13:1363-1366, Elsevier Science Ltd.

Li, S. et al., "Phosphoric Acid-Catalyzed Asymmetric Synthesis of SPINOL Derivatives", *Journal of American Chemical Society*, 2016, 138:16561-16566, American Chemical Society.

Zheng, Z. et al., "Chiral Cyclohexyl-Fused Spirobiindanes: Practical Synthesis, Ligand Development, and Asymmetric Catalysis", *Journal of American Chemical Society*, 2018, 140:10374-10381, American Chemical Society.

Wang, Y.B. et al., "Rational design, enantioselective synthesis and catalytic applications of axially chiral EBINOLs", *Nature Catalysis*, 2019, 2:504-513.

Fujisaki, S. et al., "Halogenation Using N-Halogenocompounds. I. Effect of Amines on ortho-Bromination of Phenols with NBS", *Bull. Chem. Soc. Jpn.*, May 1993, 66(5): 1576-1579, The Chemical Society of Japan.

Gnaim, J.M. et al., "Highly Regioselective ortho-Chlorination of Phenol With Sulfuryl Chloride in the Presence of Amines", *Tetrahedron Letters*, 1995, 36(22):3893-3896, Elsevier Science Ltd.

Saper, N.I. et al., "2,2,6,6-Tetramethylpiperidine-Catalyzed, Ortho-selective Chlorination of Phenols by Sulfuryl Chloride", *The Journal of Organic Chemistry*, 2014, 79:809-813, 2013 American Chemical Society.

Maddox, S.M. et al., "The Catalyst-Controlled Regiodivergent Chlorination of Phenols", *Organic Letters*, 2016, 18:5476-5479, American Chemical Society.

Xiong, X. et al., "Ammonium Salt-Catalyzed Highly Practical Ortho-Selective Monohalogenation and Phenylselenation of Phenols: Scope and Applications", *ACS Catal.*, 2018, 8:4033-4043, American Chemical Society.

Mori, K. et al., "Enantioselective Synthesis of Multisubstituted Biaryl Skeleton by Chiral Phosphoric Acid Catalyzed Desymmetrization/Kinetic Resolution Sequence", *Journal of the American Chemical Society*, 2013, 135:3964-3970, American Chemical Society.

Hurtley, A.E. et al., "Desymmetrization of Diarylmethylamido Bis(phenols) through Peptide-Catalyzed Bromination: Enantiodivergence as a Consequence of a 2 amu Alteration at an Achiral Residue within the Catalys", *The Journal of Organic Chemistry*, 2017, 82:11326-11336, American Chemical Society.

Diener, M.E. et al., "Enantioselective Synthesis of 3-Arylquinazolin-4(3H)-ones via Peptide-Catalyzed Atroposelective Bromination", *Journal of the American Chemical Society*, 2015, 137:12369-12377, American Chemical Society.

Barrett, K.T. et al., "Enantioselective Synthesis of Atropisomeric Benzamides through Peptide-Catalyzed Bromination", *Journal of the American Chemical Society*, 2013, 135:2963-2966, American Chemical Society.

Moree, W.J. et al., "Characterization of Novel Selective H1-Antihistamines for Clinical Evaluation in the Treatment of Insomnia", *Journal of Medicinal Chemistry*, 2009, 52:5307-5310, American Chemical Society.

Huang, Z. et al., "The next generation of PDE4 inhibitors", *Current Opinion in Chemical Biology*, 2001, 5:432-438, Elsevier Science Ltd.

Cheltsov, A.V. et al., "Vaccinia Virus Virulence Factor N1L is a Novel Promising Target for Antiviral Therapeutic Intervention", *J. Med. Chem.*, 2010, 53:3899-3906, American Chemical Society.

Messaoudi, S. et al., "Discovery of Isoerianin Analogues as Promising Anticancer Agents", *ChemMedChem*, 2011, 6:488-497, Wiley-VCH Verlag GmbH & Co. KGaA, Weinheim.

Mondal, S. et al., "Synthetic methodologies of achiral diarylmethanols, diaryl and triarylmethanes (TRAMs) and medicinal properties of diaryl and triarylmethanes-an overview", *RSC Advances*, 2014, 4:28317-28358, The Royal Society of Chemistry.

Paquin, J.F. et al., "Asymmetric Synthesis of 3,3-Diarylpropanals with Chiral Diene-Rhodium Catalysts", *Journal of the American Chemical Society*, 2005, 127:10850-10851, American Chemical Society.

Fessard, T.C. et al., "Enantioselective Preparation of 1,1-Diarylethanes: Aldehydes as Removable Steering Groups for Asymmetric Synthesis", *Angewandte Chemie Int. Ed.*, 2007, 46:9331-9334, Wiley-VCH Verlag Gmbh & Co., KGaA, Weinheim.

Imao, D. et al., "Cross Coupling Reactions of Chiral Secondary Organoboronic Esters With Retention of Configuration", *Journal of the American Chemical Society*, 2009, 131:5024-5025, American Chemical Society.

Tolstoy, P. et al., "Iridium-Catalyzed Asymmetric Hydrogenation Yielding Chiral Diarylmethines with Weakly Coordinating or Noncoordinating Substituents", *Journal of the American Chemical Society*, 2009, 131:8855-8860, American Chemical Society.

Woodmansee, D.H. et al., "Asymmetric hydrogenation of alkenes lacking coordinating groups", *Chem. Commun.*, 2011, 47:7912-7916, The Royal Society of Chemistry.

Taylor, B.L.H. et al., "Stereoscopic Nickel-Catalyzed Cross-Coupling Reactions of Alkyl Ethers: Enantioselective Synthesis of Diarylethanes", *Journal of the American Chemical Society*, 2011, 133:389-391, American Chemical Society.

Luan, Y. et al., "Enantioselective Addition of Boronates to o-Quinone Methides Catalyzed by Chiral Biphenols", *Journal of the American Chemical Society*, 2012, 134:19965-19968, American Chemical Society.

Do, H.Q. et al., "Nickel/Bis(oxazoline)-Catalyzed Asymmetric Negishi Arylations of Racemic Secondary Benzylic Electrophiles to Gen-

(56) References Cited

PUBLICATIONS erate Enantioenriched 1,1-Diarylalkanes", *Journal of the American Chemical Society*, 2013, 135:16288-16291, American Chemical Society.

Zhou, Q. et al., "Nickel-Catalyzed Cross-Couplings of Benzylic Pivalates with Arylboroxines: Stereoscopic Formation of Diarylalkanes and Triarylmethanes", *Journal of the American Chemical Society*, 2013, 135:3307-3310, American Chemical Society.

Yonova, I.M. et al., "Stereoscopic Nickel-Catalyzed Cross-Coupling Reactions of Alkyl Grignard Reagents and Identification of Selective Anti-Breast-Cancer Agents", *Angewandte Chemie Int. Ed.*, 2014, 53:2422-2427, Wiley-VCH Verlag Gmbh & Co., KGaA, Weinheim.

Wang, Z. et al., "Catalytic Enantioselective Intermolecular Desymmetrization of Azetidines", *Journal of the American Chemical Society*, 2015, 137:5895-5898, American Chemical Society.

Friis, S.D. et al., "Asymmetric Hydroarylation of Vinylarenes Using a Synergistic Combination of CuH and Pd Catalysis", *Journal of the American Chemical Society*, 2016, 138:8372-8375, American Chemical Society.

Konev, M.O. et al., "Intra- and Intermolecular Nickel-Catalyzed Reductive Cross-Electrophile Coupling Reactions of Benzylic Esters with Aryl Halides", *Angewandte Chemie Int. Ed.*, 2016, 55:6730-6733, Wiley-VCH Verlag Gmbh & Co., KGaA, Weinheim.

Huang, Y. et al., "Single enantiomers from a chiral-alcohol catalyst", *Nature*, Jul. 10, 2003, vol. 424, p. 146, Nature Publishing Group.

Hirashima, S.I. et al., "Development of New Chiral Brønsted Acid Catalysis", *J. Synth. Org. Chem.*, Jpn., 2013, 171(11):1116-1125.

Storer, R.I. et al., "Squaramides: physical properties, synthesis and applications", *Chem. Soc. Rev.*, 2011, 40:2330-2346, The Royal Society of Chemistry.

Zhao, Y. et al., "The M06 suite of density functionals for main group thermochemistry, thermochemical kinetics, noncovalent interactions, excited states, and transition elements: two new functionals and systematic testing of four M06-class functionals and 12 other functionals", *Theor Chem Account*, 2008, 120:215-241, Springer-Verlag 2007.

Grimme, S. et al., "Effect of the Damping Function in Dispersion Corrected Density Functional Theory", *Journal of Computational Chemistry*, 2011, 32(7): 1456-1465, Wiley Periodicals, Inc.

\* cited by examiner front view of 11a side view of 11a (the 3,5-(CF$_3$)$_2$-C$_6$H$_3$ moiety was removed for clarity)

US 11,905,237 B2

ACCESS TO CHIRAL BISPHENOL (BPOL) LIGANDS THROUGH DESYMMETRIZING ASYMMETRIC ORTHO-SELECTIVE MONO-HALOGENATION

CROSS-REFERENCE TO RELATED APPLICATION

This application claims the benefit of U.S. Provisional Application Ser. No. 63/001,929, filed Mar. 30, 2020, which is hereby incorporated by reference in its entirety including any tables, figures, or drawings.

BACKGROUND OF THE INVENTION

Catalytic asymmetric synthesis is arguably one of the most active research areas in chemistry.[1-5] Nowadays, many important drug molecules are prepared through asymmetric catalysis.[6-7] In recent decades, small-molecule catalysts have played a dominant role over enzymes in asymmetric catalysis, partly because of the ease of preparation and modification of these catalyst systems for various transformations.[8-10] Most of the practically useful catalytic enantioselective reactions, however, are rooted in a handful of privileged catalyst cores.[11-12] Some representative examples, e.g., 1,1'-bi-2-naphthol (BINOL)[13-21] and α,α,α',α'-tetraaryl-2,2-disubstituted 1,3-dioxolane-4,5-dimethanol (TADDOL)[22-23] derivatives, which are dihydroxyl compounds that serve as the cores of organocatalysts or as ligands for metal complexes, have been applied in a wide range of mechanistically unrelated reactions (FIG. 1A). A highly relevant and emerging class of privileged catalyst cores is 1,1'-spirobiindane-7,7'-diol (SPINOL), which features a spiro bisphenol system. The high structural rigidity of SPINOL gives it tremendous utility in asymmetric catalysis.[24-35] However, the cores of most SPINOL catalysts are prepared through the kinetic resolution of racemic mixtures using stoichiometric amounts of chiral resolving agents.[36-37] Tan et al. reported a seminal work on the catalytic preparation of enantiopure SPINOL skeletons, but the synthesis of substituted SPINOLs has proven somewhat challenging.[38] Ding et al. also developed an enantioselective approach towards cyclohexyl-fused SPINOL through a sequence of Ir-catalyzed asymmetric hydrogenation and spiroannulation.[39] Very recently, Tan and Houk developed a new class of 1,1'-(ethene-1,1-diyl)binaphthol scaffold and its derivatives were successfully applied in asymmetric catalysis.[40] The search for potent privileged dihydroxyl catalyst cores is still highly active, although it is well understood that identifying a new class of privileged catalyst cores is enormously difficult and often requires a certain degree of serendipity.[11-12] Herein, a new class of potent bisphenol catalyst cores through the desymmetrizing asymmetric ortho-selective mono-halogenation of phenol derivatives are described.

Organocatalysis provides a promising opportunity for the ortho-halogenation of phenols, and the resulting ortho-halogenated phenols are prevalent precursors for catalyst modification.[41-45] However, the ortho-halogenation of phenols in asymmetric synthesis has been sporadic. Akiyama and co-workers described an interesting approach in the desymmetrization/kinetic resolution of biaryl phenol derivatives 'through asymmetric ortho-bromination (FIG. 1B).[46] Recently, Miller and co-workers reported a seminal work on designing tailor-made peptide catalysts, which were found to be highly specific in the ortho-bromination/desymmetrization of diarylmethylamido bisphenols 3 to give 4a with good enantioselectivity. However, the yields were moderate as a result of the poor mono/dibromination (4a/4b) selectivity.[47-49] Nonetheless, these works inspired us to consider the desymmetrization of bisphenol system 5 through asymmetric organocatalytic ortho-halogenation. Moreover, the subjective invention approach to the preparation of chiral diarylmethine compounds could be potentially useful in drug discovery and natural product synthesis,[50-54] as has been demonstrated by several elegant catalytic desymmetrization methodologies.[55-67]

BRIEF SUMMARY OF THE INVENTION

An embodiment of the invention is directed to the halogenation of phenols catalytic asymmetric ortho-selective mono-halogenation of bisphenols using a stoichiometric amount of a source of an achiral electrophilic halogen (e.g., bromine), which can selectively halogenate one of the enantiotopic phenol moieties to give halogenated phenol compounds such as, for example, compound 6. The point-chirality and the halogen handle can be introduced simultaneously (FIG. 1C). The bulky substituent at the stereogenic center can restrict the rotation of the phenols, furnishing a rigid bisphenol system potentially useful as a catalyst core.

In certain embodiments, ortho-halogenation of the monohalogenated phenol, such as compound 6, with a source of a halogen (e.g. chlorine) results in a bisphenol with two halogen handles, such as, for example, compound 7. In certain embodiments, the two halogens can have different reactivity towards cross-coupling.

In certain embodiments, the halogen handles at the ortho-positions of the phenol could readily be modified through cross-coupling to give substituted phenol, such as, for example 8a, 8b, or 8c. The substituted phenol is defined by the substituting of the halogen handles by other chemicals. In some embodiments, this substitution enables various substituents to be introduced in close proximity to the OH. This strategy creates novel catalysts.

BRIEF DESCRIPTION OF THE DRAWINGS

(FIG. 1A) Privileged catalyst scaffolds containing dihydroxyl moieties. (FIG. 1B) Examples from the literature of desymmetrization of phenols through asymmetric ortho-halogenation. (FIG. 1C) The design for the preparation of potent chiral bisphenol catalyst core through desymmetrizing asymmetric ortho-halogenation.

(FIG. 5A) Preparation of chiral phosphoric acids 11 using bisphenol core 6. (FIG. 5B) DFT-calculated geometry of 11a. (FIG. 5C) Asymmetric addition of indole to imine catalyzed by chiral phosphoric acids 11. (FIG. 5D) Chiral phosphoric acid 11a-catalyzed Biginelli reaction among 15, 16, and 17. (FIG. 5E) Preparation of chiral ligand 19 and addition of diethyl zinc to 20. Conditions: (a) iPr$_2$NH$_2$Cl (5 mol %), 1,3-dichloro-5,5-dimethylhydantoin (DCDMH), toluene, 0° C., 2 h; (b) Ar$^1$—B(OH)$_2$, Pd(PPh$_3$)$_4$ (6 mol %), Na$_2$CO$_3$ (aq.), toluene/EtOH (2:1 v/v), reflux, 24 h (11a, Ar$^1$=1-naphthyl; 11b, Ar$^1$=3,5-bis(trifluoromethyl) phenyl; 11c, Ar$^1$=4-nitrophenyl); (c) Ar$^2$—B(OH)$_2$, Pd(OAc)$_2$ (6 mol %), S-Phos (12 mol %), K$_3$PO$_4$, THF, 80° C., 18 h (11a, Ar$^2$=2-naphthyl; 11b, Ar$^2$=1-naphthyl; 11c, Ar$^2$=1-naphthyl); (d) POCl$_3$, pyridine, reflux, 3 h, then H$_2$O, reflux 3 h. (e) NaH, MeI, DMF, 23° C., 12 h; (f) nBuLi, EtI, THF, −78° C., 12 h; (g) BBr$_3$, CH$_2$Cl$_2$, 23° C., 12 h; (h) (+)-bis[(R)-1-phenylethyl]amine, PCl$_3$, Et$_3$N, THF, −78-23° C., 24 h.

(FIG. 6A) Ortho-bromination of mono-methylated bisphenol rac-22. (FIG. 6B) Attempt to halogenate 24 with catalyst 9d. (FIG. 6C) Ortho-bromination of 5a with excess NBS.

(FIG. 7A) Energy profile of WAY-1 towards (S)-6a. (FIG. 7B) Optimized geometries of the intermediates and transition states.

DETAILED DISCLOSURE OF THE INVENTION

Figure 1A:
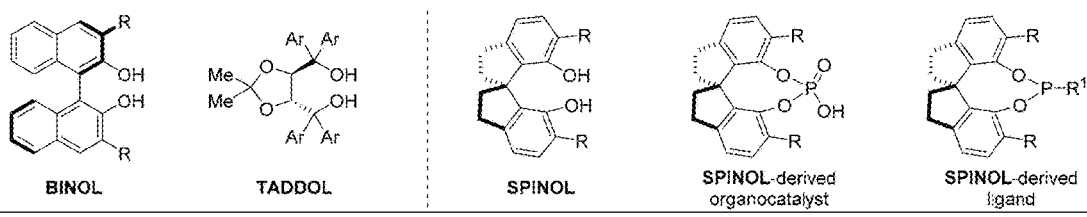
FIGS. 1A-1C. Design of privileged dihydroxyl catalyst cores.
Figure 1B:
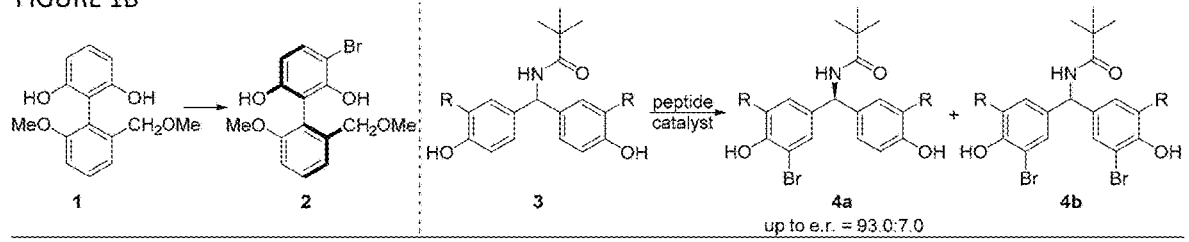
Figure 1C:
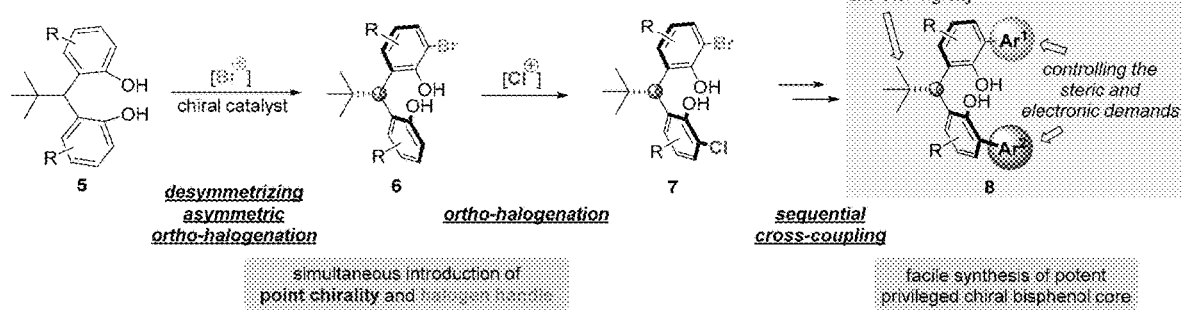

Asymmetric catalysis plays a central role in the synthesis of new drugs and novel functional materials. Many of the asymmetric reactions rely on catalysts derived from a few privileged cores such as dihydroxyl compounds. Thus, discovery of new potent privileged dihydroxyl catalyst cores is still highly sought after, but it is well-understood that identifying a new class of privileged catalyst cores is enormously difficult. The subject invention describes desymmetrizing asymmetric halogenation of bisphenols to prepare to a new class of chiral halo-bisphenols. The halogen handles can be modified at late-stage through cross-coupling so that various potent privileged dihydroxyl catalyst cores can be prepared. These catalyst cores can be converted into chiral phosphoric acid for organocatalysis and used as phosphoramidite ligand in metal catalysis.

The subject invention provides for a novel halogenation process for preparing halogenated phenols. The novel process comprises contacting a phenol, a mono-halogenated phenol, or a mixture thereof, the aforementioned compound(s) being referred to in various places hereinafter as the "reactant phenol," with a source of halogen in the presence of a catalyst under process conditions sufficient prepare a halogenated phenol having a greater number of halogen substituents as compared with the reactant hydrocarbon.

In certain embodiments of the invention, the catalyst used in the process of this invention comprises amino organocatalysts. The amino organocatalyst can be bifunctional, wherein a bifunctional molecule is defined as one that has two functional groups. In certain embodiments, the amino organocatalysts can be an amino-urea catalyst. In certain embodiments, the amino organocatalysts can be an amino-squaramide catalyst. The catalysts can have various functional groups that can include an N,N-dimethylamine unit, an N,N-di-n-pentyl group, an (S)-BINOL-amine derivative, or an (R)-BINOL-amine substituent. Exemplary amino organocatalysts, 9a (N-[3,5-bis(trifluoromethyl)phenyl]-N'-[(1S,2S)-2-(dimethylamino)cyclohexyl]urea), 9b (N-[3,5-bis(trifluoromethyl)phenyl]-N'-[(1S,2S)-2-(di-n-pentylamino)cyclohexyl]urea), 9c (3-[[3,5-bis(trifluoromethyl)phenyl]amino]-4-[[(1S,2S)-2-(dimethylamino)cyclohexyl]amino]-3-cyclobutene-1,2-dione), 9d (N-[3,5-bis(trifluoromethyl)phenyl]-N'-[(1S,2S)-2-[(11bS)-3,5-dihydro-4H-dinaphth[2,1-c:1',2'-e]azepin-4-yl]cyclohexyl]urea), or 9e N-[3,5-bis(trifluoromethyl)phenyl]-N'-[(1S,2S)-2-[(11bR)-3,5-dihydro-4H-dinaphth[2,1-c:1',2'-e]azepin-4-yl]cyclohexyl]urea), are demonstrated in FIG. 2. In certain embodiments, the concentration of the catalyst can be at least 0.1 mol %, 1 mol %, 2 mol %, 2.5 mol %, 3 mol %, 3.5 mol %, 4 mol %, 4.5 mol %, 5 mol %, 5.5 mol %, 6 mol %, 6.5 mol %, 7 mol %, 7.5%, 10 mol %, or greater.

The novel halogenation process of this invention advantageously converts a reactant phenol into a halogenated phenol product having an increased number of halogen substituents as compared with the reactant phenol. The halogenated phenols can be meta-halogenated, para-halogenated, or, in preferred embodiments, the halogenated phenols are ortho-halogenated. In preferred embodiments, the reactant phenol is a bisphenol. Examples of bisphenols that can be used are bisphenol A, bisphenol AP, bisphenol, AF, bisphenol B, bisphenol BP, bisphenol C, bisphenol C2, bisphenol E, bisphenol F, bisphenol G, bisphenol M, bisphenol S, bisphenol P, bisphenol PH, bisphenol TMC, bisphenol Z, dinitrobisphenol A, tetrabromobisphenol A, or, preferably, 5a, 5b, 5c, 5d, 5e, 5f, 5g, 5h, 5i, 5j, 5k, 5l, 5m, 5n, 5o, 5p, and 5q, as demonstrated in FIGS. 2 and 3. Examples of mono-halogenated bisphenols that can be the reactant phenol are 6a, 6b, 6c, 6d, 6e, 6f, 6g, 6h, 6i, 6j, 6k, 6l, 6m, 6n, 6o, 6p, and 6q, as demonstrated FIG. 3 and 10a, 10b, 10c, 10d, 10e, 10f, 10g, 10h, 10i, and 10j, as demonstrated in FIG. 4. In certain embodiments, the concentration of the reactant phenol can be at least 0.01 mmol, 0.05 mmol, 0.1 mmol, 0.15 mmol, 0.2 mmol, 0.25 mmol, 0.3 mmol, 0.35 mmol, 0.4 mmol, 0.45 mmol, 0.5 mmol, 1 mmol or greater. Additionally, the process of the subjection invention can be performed on different scales such as, for example, 0.1 mmol, 0.5 mmol, 1.0 mmol, 5 mmol, or 10 mmol. The process of the subject invention may be conducted in "fuel-rich" conditions, in which there is an excess of the phenol reactant, but the process is not limited to "fuel-rich" modes.

In the process of this invention, the source of halogen may be provided, for example, as elemental halogen, hydrogen halide, or any electrophilic halogen chemical, including any inorganic or organic halogen-containing compound or mixture of such compounds that is capable of transferring its halogen atom(s) to the reactant phenol. Suitable, non-limiting examples of a source of halogen include bromine, N-bromosuccinimide (NBS), N-bromophthalimide (NBP), N-bromoacetamide (NBA), 1,3-dibromo-5,5-dimethylhydantoin (DBDMH), 1,3-dibromo-5,5-diphenylhydantoin (DBDPH), 2,4,4,6-tetrabromo-2,5-cyclohexadienone (TBCO), chlorine, N-chlorosuccinimide (NCS), N-chlorophthalimide (NCP), 1,3-dichloro-5,5-dimethylhydantoin (DCDMH), 1,3-dichloro-5,5-diphenylhydantoin (DCDPH), 1-(4-methylbenzoyl)-3-chloro-5,5-diphenylhydantoin, iodine, and N-iodosuccinimide The source of halogen may be provided in any amount that is effective in producing the desired halogenated phenol product. Typically, the amount of halogen source will vary depending upon the specific process stoichiometry, the reactor design, and safety considerations. It is possible, for example, to use a stoichiometric amount of halogen source with respect to the reactant phenol. Alternatively, the source of halogen may be used in an amount that is greater or less than the stoichiometric amount, if desired. In preferred embodiments, the source of halogen may be used in a stoichiometric amount. In certain embodiments, the concentration of the source of the halogen can be at least 0.01 mmol, 0.05 mmol, 0.1 mmol, 0.15 mmol, 0.2 mmol, 0.21 mmol, 0.25 mmol, 0.3 mmol, 0.35 mmol, 0.4 mmol, 0.45 mmol, 0.5 mmol, 1 mmol or greater.

In certain embodiments, the process of the subject invention can comprise the addition of the reactant phenol, source of halogen, and catalyst to a solvent. The solvent can be, but not limited to, a hydrocarbon or aromatic hydrocarbon, which includes benzene, xylenes, halobenzene, hexanes, dichloromethane, 1,2-dichloroethane, tetrachloromethane, or, preferably, toluene. Additionally, other compounds can be added to the solvent. The ratio of the solvent to the added compound can be at least 1:1, 2:1, 3:1, 4:1, 5:1, 6:1, 7:1, 8:1, 9:1, 10:1, or greater. An example of a compound that can be added to the solvent includes carbon tetrachloride ($CCl_4$). The solvent or solvent/added compound mixture can be present at a concentration of at least 50%, 60%, 70%, 75%, 80%, 85%, 86%, 87%, 88%, 89% 90%, 91%, 92%, 93%, 94%, 95%, 96%, 97%, 98%, 99%, or greater concentration.

In certain embodiments, the reaction is performed at a temperature of at least −80° C., −78° C., −60° C., −40° C., −25° C., −20° C., 0° C., 20° C., 23° C., 25° C., 80° C. or greater. In preferred embodiments, the process can be performed at a temperature less than or equal to −40° C. The temperature can be determined by a variety of factors including reaction time, reagent concentrations, and desired products and/or product concentrations. In certain embodiments, the halogenation, including bromination and chlorination, of the reactant phenol can be performed at a different temperature than subsequent steps, including a subsequent halogenation of a mono-halogenated phenol or cross-coupling reactions.

In certain embodiments, a molecular sieve (M.S.) is used. The M.S. can have a pore size of about 0.1 Å to about 100 Å, about 1 Å to about 10 Å, or about 4 Å.

In certain embodiments, the reactions of the subject invention can be performed for at least 1 hour, 2 hours, 3 hours, 4 hours, 8 hours, 12 hours, 24 hours, 2 days, 3 days, 4 days, 5 days, 6 days, 7 days, 10 days or longer. The length of time can be determined by a variety of factors including temperature, reagent concentrations, and desired products and/or product concentrations. In certain embodiments, the halogenation, including bromination and chlorination, of the reactant phenol can be performed for a different amount of time in subsequent steps, including a subsequent halogenation of a mono-halogenated phenol or cross-coupling reactions.

In certain embodiments, the yield of halogenated phenols has an enantiomeric ratio (e.r.) of at least 50:50, 59.5:40.5 67.5:32.5, 79.5:20.5, 83.5:16.5, 88:12, 93:7, 94:6, 95:5, 95.5:4.5, 96:4, 96.5:3.5, 97:3, 97.5:2.5, 98:2, 98.5:1.5, 99:1, 99.2:0.8, 99.5:0.5, or greater.

In certain embodiments, the yield of halogenated phenols is at least 50%, 60%, 70%, 75%, 80%, 85%, 90%, 91%, 92%, 93%, 94%, 95%, 96%, 97%, 98%, 99%, or greater.

The halogenated phenol that is produced by certain embodiments of the subject invention is an asymmetric halogenated phenol. The asymmetric halogenated phenol can be mono-halogenated or bihalogenated. The mono-halogenated phenol can be processed according to the subject invention to create the asymmetric bihalogenated phenol. The bihalogenated phenols can have two different halogens, such as, for example, chloride and bromide. The bulky substituent at the stereogenic center could restrict the rotation of the phenols, furnishing a rigid bisphenol system potentially useful as a catalyst core. The halogenated phenols can be can meta-halogenated, para-halogenated, or, in preferred embodiments, the halogenated phenols are ortho-halogenated. In certain embodiments, the prepared halogenated phenol is a chiral halogenated bisphenol; preferably, the chiral halogenated bisphenol has point chirality.

Figure 5A:
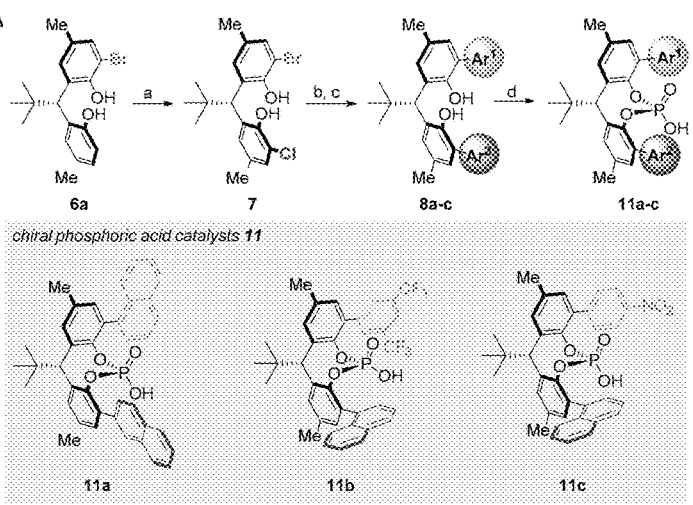
FIGS. 5A-5E. Application of the bisphenol core in asymmetric catalysis.

The novel halogenation process, described hereinabove, may be beneficially integrated with downstream processes to use phenols with a halogen handle in cross-coupling reactions. The phenols can have at least one halogen handle or two halogen handles. In certain embodiments, the halogen handles at the ortho-positions of the bisphenol could readily be modified through cross-coupling to prepare a substituted bisphenol. The substituted bisphenol is defined by the substituting of the halogen handles by other chemicals such as, for example, boronic acids. In certain embodiments, the two halogens can have different reactivity towards cross-coupling. The cross-coupling reaction uses additional reagents. The reagents include acids, such as, for example, 1-naphtyl and 2-naphthyl boronic acids, salt such as, for example, sodium carbonate and tripotassium phosphate, and a solvent, such as for example toluene and ethanol. In certain embodiments, the cross coupling reaction further comprises S-Phos, present in a concentration of at least 0.1 mol %, 1 mol %, 2 mol %, 2.5 mol %, 3 mol %, 3.5 mol %, 4 mol %, 4.5 mol %, 5 mol %, 5.5 mol %, 6 mol %, 6.5 mol %, 7 mol %, 7.5%, 10 mol %, or greater. In certain embodiments, the cross-coupling reaction further comprises tetrahydrofuran (THF) at a concentration of about 0.01M to about 10M, about 0.1M to about 5.0M, or about 0.2M to about 1.0M. In certain embodiments, the acids are present in a concentration of at least 0.1 mol %, 1 mol %, 2 mol %, 2.5 mol %, 3 mol %, 3.5 mol %, 4 mol %, 4.5 mol %, 5 mol %, 5.5 mol %, 6 mol %, 6.5 mol %, 7 mol %, 7.5%, 10 mol %, or greater. In certain embodiments, the ratio of toluene to ethanol can be at least 1:1, 2:1, 3:1, 4:1, 5:1, 6:1, 7:1, 8:1, 9:1, 10:1, or greater. The chemical reagents in the cross-coupling reaction can be processed by reflux for about 2 hours to about 48 hours, about 8 hours to about 36 hours, or about 18 hours to about 24 hours. In certain embodiments, the cross-coupling reaction is performed at a temperature of at least −80° C., −78° C., −60° C., −40° C., −25° C., −20° C., 0° C., 20° C., 23° C., 25° C., 80° C. or greater. In certain embodiments, the cross-coupling reaction is performed in stages in which chemical reactants are added or removed; additionally, the temperature or reaction time is changed throughout the process. An example of cross-coupling reaction in which the halogenated phenol 7 can be used is palladium-catalyzed cross-coupling with 1-naphtyl and 2-naphthyl boronic acids at the aryl bromide and chloride, respectively, to give substituted bisphenol 8a, 8b, or 8c, as demonstrated in FIG. 5A.

In certain embodiments, the substituted phenols, such as, for example 8a, 8b, or 8c, can be further processed to yield a dihydroxyl catalyst. In preferred embodiments, the dihydroxyl catalyst is a chiral phosphoric acid catalyst that is prepared using oxophosphorus trichloride and pyridine, refluxed for about 1 hour to about 12 hours, about 2 hours to about 8 hours, or about 3 hours, water is then added to the reaction and the composition is then refluxed again for about 1 hour to about 12 hours, about 2 hours to about 8 hours, or about 3 hours. This process yields the chiral phosphoric acid catalysts 11a, 11b, or 11c, as demonstrated in FIG. 5A.

In certain embodiments the dihydroxyl catalysts, such as, for example the chiral phosphoric acid catalysts 11a, 11b, or 11c, can catalyze asymmetric reactions. In preferred embodiments, the dihydroxyl catalysts can catalyze the addition of indoles to imines to give a corresponding adduct. In certain embodiments, the dihydroxyl catalyst is present at a concentration of at least 0.1 mol %, 1 mol %, 2 mol %, 2.5 mol %, 3 mol %, 3.5 mol %, 4 mol %, 4.5 mol %, 5 mol %, 5.5 mol %, 6 mol %, 6.5 mol %, 7 mol %, 7.5%, 10 mol %, or greater. In certain embodiments, a halogenated hydrocarbon such as, for example, $(CH_2Cl)_2$ is used in the catalysis reaction at a concentration of about 0.001M to about 10M, about 0.0025M to about 2.5M, about 0.01M to about 1.0M, about 0.025M to about 0.25M, or about 0.025M to about 0.1M. The e.r. of the resulting adduct can be up to 98.0:2.0 e.r. In certain embodiments, the reaction is performed at a temperature of at least −80° C., −78° C., −60° C., −40° C., −25° C., −20° C., 0° C., 20° C., 23° C., 25° C., 80° C. or greater for about 30 mins to about 24 hours, about 1 hour to about 18 hours, or about 2 hours to about 12 hours.

In certain embodiments the dihydroxyl catalysts, such as, for example chiral phosphoric acid catalysts 11a, 11b, or 11c, can also be used to catalyzing a Biginelli reaction, preferably, using aldehyde, urea, and ethyl acetoacetate to prepare 3,4-dihydropyrimidin-2(1H)-one. In certain embodiments, the dihydroxyl catalyst is present in a concentration of at least 0.1 mol %, 1 mol %, 2 mol %, 2.5 mol %, 3 mol %, 3.5 mol %, 4 mol %, 4.5 mol %, 5 mol %, 5.5 mol %, 6 mol %, 6.5 mol %, 7 mol %, 7.5%, 10 mol %, or greater. In certain embodiments, the aldehyde, urea, or ethyl acetoacetate is present in a concentration of 0.001M to about 10M, about 0.0025M to about 2.5M, about 0.01M to about 1.0M, about 0.025M to about 0.25M, or about 0.025M to about 0.1M. In certain embodiments, a halogenated hydrocarbon such as, for example $(CH_2Cl)_2$ is used in the catalysis reaction at a concentration of 0.001M to about 10M, about 0.0025M to about 2.5M, about 0.01M to about 1.0M, about 0.025M to about 0.25M, or about 0.025M to about 0.1M. In certain embodiments, the reactions of the subject invention can be performed for at least 1 hour, 2 hours, 3 hours, 4 hours, 8 hours, 12 hours, 24 hours, 2 days, 3 days, 4 days, 5 days, 6 days, 7 days, 10 days or longer. In certain embodiments, the reaction is performed at temperature of at least −80° C., −78° C., −60° C., −40° C., −25° C., −20° C., 0° C., 20° C., 23° C., 25° C., 80° C. or greater. In preferred embodiments, the process can be performed at a temperature of −20° C. or 25° C.

In certain embodiments the novel halogenation process, described hereinabove, may be beneficially integrated with downstream processes to use phenols with a halogen handle in metal catalysis. In preferred embodiments, a phosphoramidite ligand can be prepared from a halogenated phenol using a series of reactions. In the first reaction, NaH, MeI, DMF, are contacted to the halogenated phenol at a temperature of about 0° C. to about 25° C. or about 23° C. for about 8 hours to about 24 hours or about 12 hours. In the second reaction, n-BuLi, EtI, THF are contacted to the products of the first reaction at a temperature of about −78° C. to about 23° C. for about 2 hours to about 24 hours, about 4 hours to about 18 hours, or about 8 hours to about 12 hours. In the third reaction, $BBr_3$ and $CH_2Cl_2$ are contacted to the products of the second reaction at a temperature of about 20° C. to about 25° C. or about 23° C. for about 8 hours to about 24 hours or about 12 hours. In the fourth reaction, (+)-bis [(R)-1-phenylethyl]amine, $PCl_3$, $Et_3N$, and THF are contacted to the products of the third reaction at a temperature of about −80° C. to about 80° C. or about −78° C. to about 23° C. for about 8 hours to about 48 hours or about 24 hours.

The halogenated phenols produced according to the subject invention could be potential privileged cores, and open a new avenue for the design and application of bisphenol catalysts.

In some embodiments, this substitution of halogens for other chemicals enables various substituents to be introduced in close proximity to the OH. This is of particular importance to catalyst design because it is believed that close communication between the substituents and the phenol moiety can effectively shape the reaction pocket. In addition, this strategy allows for late-stage modification of the bisphenol ligands so that a large library of analogues can easily be accessed. Moreover, this approach to the preparation of chiral diarylmethine compounds could be potentially useful in drug discovery and natural product synthesis.

Definitions

As used herein, the singular forms "a," "an," and "the" are intended to include the plural forms as well, unless the context clearly indicates otherwise. To the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise;" "consisting essentially of" and "consists essentially of;" and "consisting" and "consists" can be used interchangeably though each retains its traditional legal meaning.

The phrases "consisting essentially of" or "consists essentially of" indicate that the relevant description or claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Typically, the term "about" indicates that the relevant parameter is within the range of 0 to 10% of a given value.

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are intended to be explicitly included.

As used herein, the "enantiomeric ratio" or "e.r." is the ratio of product of the reaction to the starting reactant.

As used herein, "halogenation" us the replacement of one or more hydrogen atoms in an organic compound by a halogen. A "halogen" is defined as fluorine, chlorine, bromine, or iodine. As used herein, "chlorination" is the halogenation using a chlorine-containing chemical. As used herein, "bromination" is the halogenation using a bromine-containing chemical.

As used herein, a "cross-coupling reaction" is a reaction in which two different starting materials, each of which is usually endowed with an activating group, are reacted together using a catalyst. The cross-coupled reaction can result in the loss of the activating groups and a new covalent bond between the remaining fragments.

As used herein, "fuel-rich" refers to an excess of a chemical reactant.

As used herein, an "adduct" is the product of an addition of two or more distinct molecules.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 1—Reaction Optimization

Figure 2:
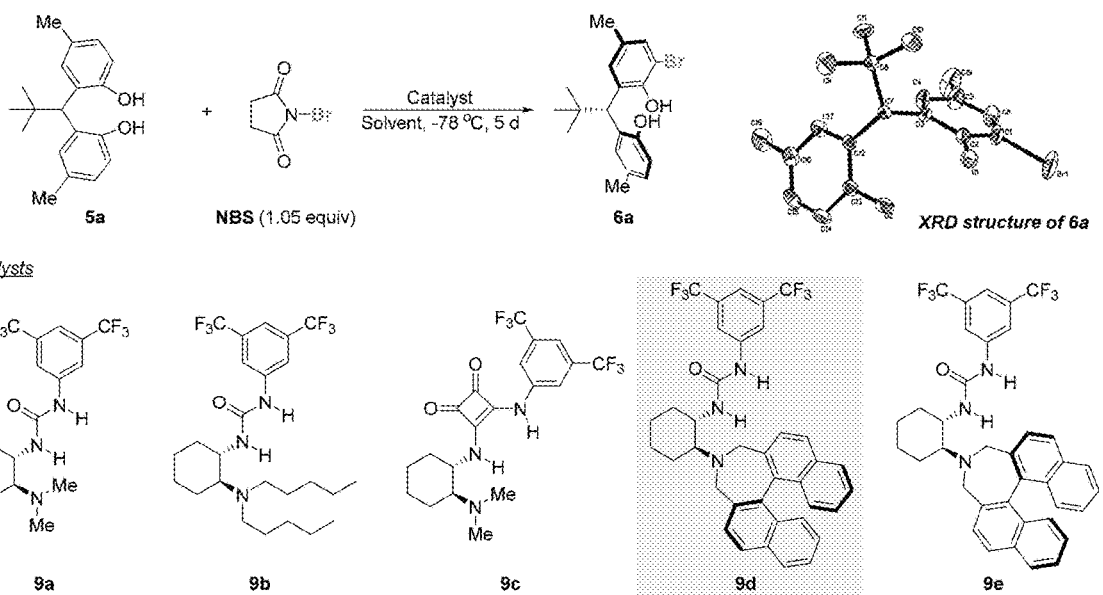
FIG. 2. Optimization of the desymmetrizing asymmetric ortho-halogenation of bisphenol. Conditions: the reactions were conducted with 5a (0.2 mmol), catalyst 9, and NBS (0.21 mmol) in the indicated solvent at −78° C. for 5 d in the absence of light. Footnotes: *The reaction was conducted at 1.0 mmol scale. †The reaction was conducted at 5 mmol scale. ‡Recrystallized from hexanes. Me, methyl; e.r., enantiomeric ratio; MS, molecular sieves.

Halogenation of symmetrical bisphenol 5a was examined using N-bromosuccinimide (NBS) as the halogen source. It was rationalized that the acidity of the hydroxyl proton could be enhanced through intramolecular hydrogen bond.[68-69] It is envisioned that an amino organocatalyst could activate the halogen source and the phenol substrate (through hydrogen bond with the acidic proton) simultaneously, and enantioselectively deliver the halogen atom.[70] Thus, various bifunctional amino-urea catalysts 9 were examined (FIG. 2). Amino-urea 9a bearing an N,N-dimethylamine unit could desymmetrize 5a to give 6a in promising enantiomeric ratio (e.r.) of 67.5:32.5 (entry 1). Changing the amine from an N,N-dimethyl to an N,N-di-n-pentyl group (catalyst 9b) significantly improved the e.r. of 6a (entry 2). Considerable diminishment of the reaction efficiency and enantioselectivity was encountered when replacing the urea moiety with a squaramide (catalyst 9c) (entry 3).[71] A lower reactant concentration favored the desymmetrization of 5a (entry 4). Both the reaction yield and e.r. of 6a were dramatically improved when a 4 Å molecular sieve (MS) was used as an additive (entry 5). A 91% yield and 97.5:2.5 e.r. of the desired product 6a were obtained after fine-tuning the reaction media (entry 6). Further modification of the catalyst by introducing an (S)-BINOL-amine derivative (i.e., catalyst 9d) gave rise to 6a in excellent e.r. (entry 7). The chirality of the BINOL core was found to be crucial and the yield of 6a diminished significantly when using the mismatched catalyst 9e bearing the (R)-BINOL-amine substituent (entry 8). The reaction was readily scalable at 1 mmol or 5 mmol scale using 2.5 mol % of 9d as the catalyst (entries 9 and 10). An enantiopure sample of 6a could be obtained by a simple recrystallization, which is important for preparing chiral bisphenol cores for other catalytic applications (vide infra). The absolute configuration of 6a was confirmed unambiguously by X-ray crystallography.

Example 2—Desymmetrizing Asymmetric Ortho-Bromination of Biphenols

Figure 3:
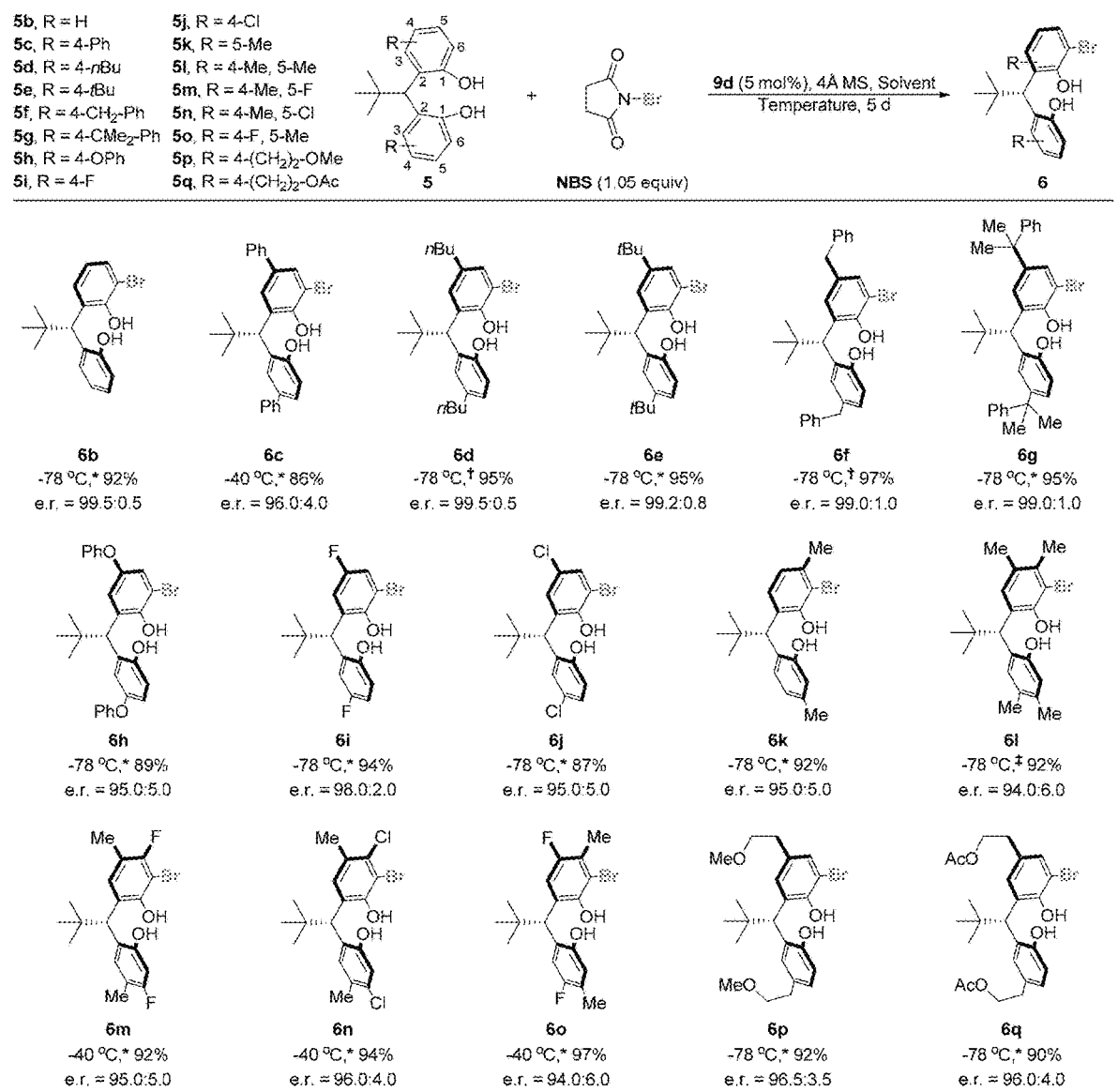
FIG. 3. Desymmetrizing asymmetric ortho-selective mono-bromination of bisphenol 5. Conditions: the reactions were conducted with 5 (0.1 mmol), catalyst 9d (5 mol %), NBS (0.105 mmol), and 4 Å MS in the indicated solvent (4 mL) and temperature for 5 d in the absence of light. Footnotes: *In toluene/CCl$_4$ (2:1 v/v). † In toluene/CCl$_4$ (5:1 v/v). ‡In toluene. Ph, phenyl; nBu, n-butyl; Me, methyl; Ac, acetyl.
Figure 4:
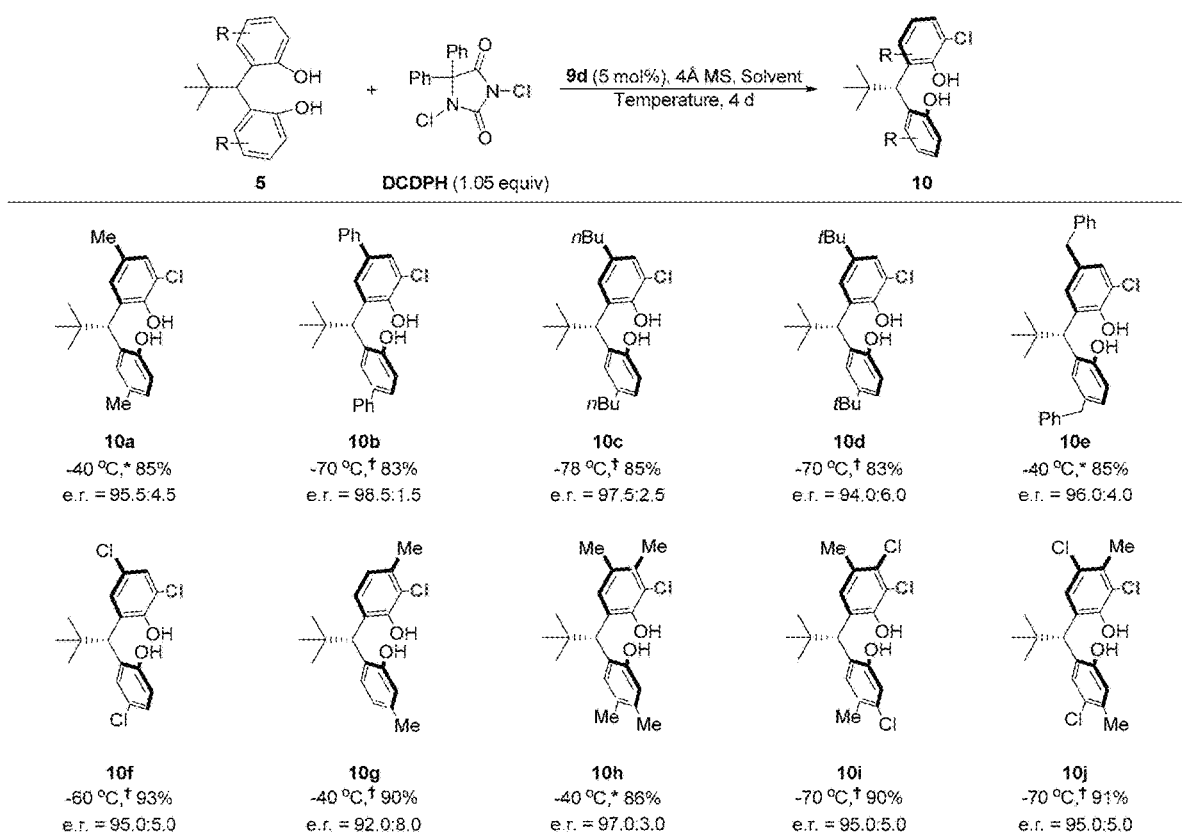
FIG. 4. Desymmetrizing asymmetric ortho-selective mono-chlorination of bisphenol 5. Conditions: the reactions were conducted with 5 (0.1 mmol), catalyst 9d (5 mol %), DCPDH (0.105 mmol), and 4 Å MS in the indicated solvent (4 mL) and temperature for 4 d in the absence of light. Footnotes: *In toluene. † In toluene/CCl$_4$ (2:1 v/v).

Next, the substrate scope was examined (FIG. 3). The reaction worked well with 5b bearing no substituent at the 4-position, giving 6b in 92% yield and 99.5:0.5 e.r. The strong preference of the ortho-bromination at the phenol suggested that the hydroxyl unit in 5 might be crucial in directing the halogenation (vide infra). A range of alkyl- or aryl-substituted substrates 5c-5g were examined and the corresponding ortho-brominated product 6b-6g were obtained in good-to-excellent e.r. Bisphenol 5h with ether at the 4-position of the phenol moiety was also compatible, giving product 6h smoothly. Substrates 5i and 5j with electron-withdrawing substituents also gave the desired mono-brominated products 6i and 6j with high efficiency and enantioselectivity. 3-Substituted bisphenol 5k furnished 6k smoothly. A range of multisubstituted substrates 5l-5o were also ortho-brominated smoothly using the catalytic protocol, and good e.r. of 6l-6o were obtained. Moreover, functional groups including methyl ether and acetate (5p and 5q) were tolerated under the reaction conditions.

Example 3—Application of Bisphenol as a Catalyst Core

To explore the potential of bisphenol 6 as a potent catalyst core, 6 was further functionalized by introducing various substituents in close proximity to the hydroxyl groups. Thus, 6a was ortho-chlorinated to give 7 in excellent yield (FIG. 5A).[41-45] Compound 7 contains two halogen handles that have different reactivity towards cross-coupling reactions. For instance, 7 could undergo consecutive palladium-catalyzed cross-coupling with 1-naphthyl and 2-naphthyl boronic acids at the aryl bromide and chloride, respectively, to give substituted bisphenol 8a. By the same strategy, substituted bisphenols 8b and 8c, which have different steric and electronic demands, could readily be prepared. This strategy allows a fast access to a library of chiral bisphenol ligands.

Figure 5B:
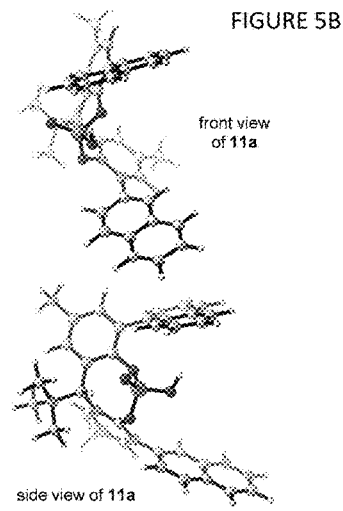
Figure 5C:
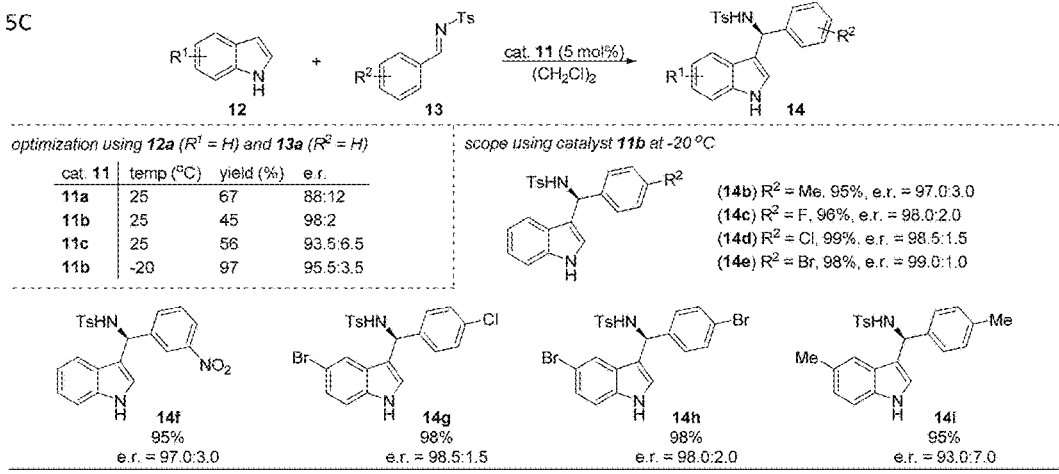
Figure 5D:
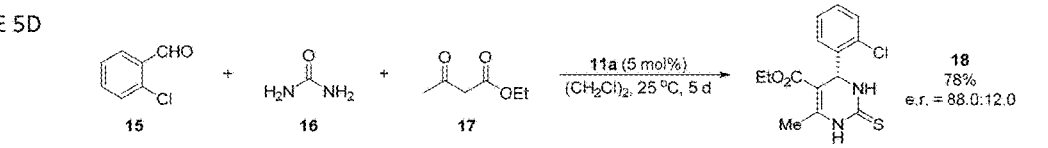
Figure 5E:
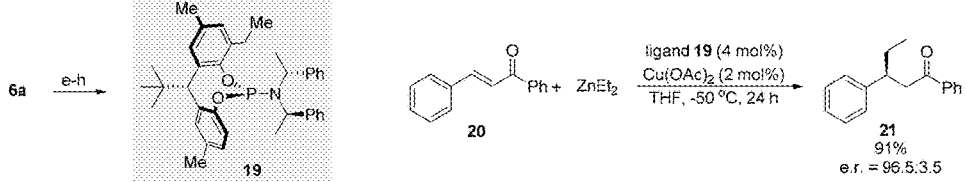

Then, chiral phosphoric acids were prepared using the bisphenol cores 8 to evaluate the asymmetric performance. Treatment of bisphenols 8a-8c with oxophosphorus trichloride gave chiral phosphoric acid catalysts 11a-11c. Based on the density functional theory (DFT) calculation on 11a, an optimized geometry with a structurally well-defined phosphoric acid catalyst pocket was identified (FIG. 5B). The calculation also showed that the geometry resembled that of the SPINOL system.[32-35] Experimentation indicated that chiral phosphoric acid 11a could catalyze by activating imine 13 via hydrogen bond interaction between 11a and 13. The asymmetric addition of indole 12 to imine 13 to give the corresponding adduct 14 with appreciable enantioselectivity (FIG. 5C). Further screening other catalysts 11b and 11c with substituents that have different steric and electronic demands, the enantioselectivity of 14 could be enhanced dramatically to 98.0:2.0 e.r. (using 11b). The yield of 14a could be improved by decreasing the reaction temperature. The reaction was compatible with a range of substituted indoles 12 and imine partners 13, giving products 14b-14j in excellent yields and e.r. Catalyst 11a was also found to be potentially useful in catalyzing the Biginelli reaction among aldehyde 15, urea (16), and ethyl acetoacetate (17), giving 3,4-dihydropyrimidin-2(1H)-one 18 smoothly (FIG. 5D). Additionally, the possibility of applying the bisphenol core in metal catalysis was explored. Phosphoramidite ligand 19a was readily prepared from 6a. Ligand 19 together with copper (II) triflate could catalyze the enantioselective addition of diethyl zinc to chalcone 20 to give 21 in good yield and e.r. (FIG. 5E). It was also found that performance of the bisphenol catalysts were superior to the state-of-the-art BINOL-derived catalysts (11d, 11e, 19b) and SPINOL-derived catalysts (11f, 11g, 19c) in the abovementioned reactions. These results suggest that bisphenols 6 and 8 could be potential privileged cores, and open a new avenue for the design and application of bisphenol catalysts.

Example 4—Mechanistic Studies

Figure 6A:
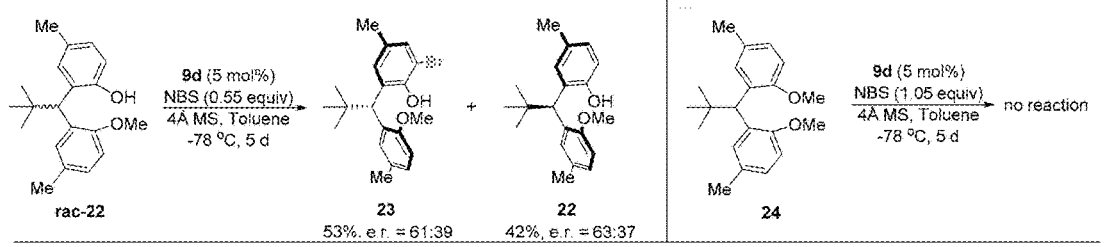
FIGS. 6A-6C. Control experiments.
Figure 6B:
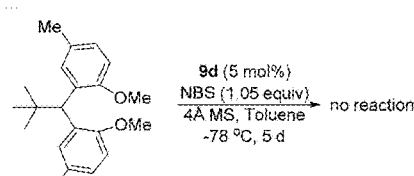

Several control experiments were conducted to shed light on the reaction mechanism. Firstly, mono-O-methylated substrate racemic-22 was prepared and subjected to the ortho-halogenation. The reaction was found to be sluggish and gave product 23 and enantioenriched 22 with low enantioselectivity (FIG. 6A). When the same reaction conditions were applied to the di-O-methylated substrate 24, no reaction was observed and the starting material was recovered quantitatively (FIG. 6B). It was speculated that the two phenol moieties in 5 might work synergistically to achieve the enantioselective mono-ortho-halogenation. Based on the data from the crystallographic analysis of 6a, it appears that the two oxygen atoms were linked through an intramolecular hydrogen bond. A $^1$H NMR experiment in which the catalyst was mixed with the halogen source NBS was also conducted. The protons adjacent to the tertiary amine's nitrogen exhibited a significant downfield shift. It was speculated that the amine might coordinate to the electrophilic Br while the succinimide anion might form hydrogen bonds to the urea moiety.

Figure 6C:
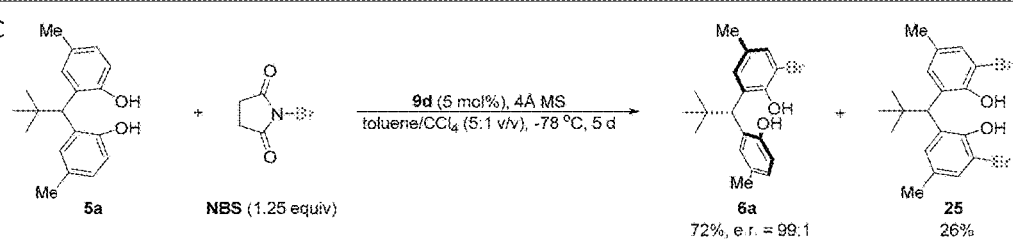

When excess NBS was used, the e.r. of the mono-brominated product 6a was unchanged but the yield of the dibrominated product 25 increased (FIG. 6C). This result indicates that the second step of bromination is unlikely to be a kinetic resolution and the high enantioselectivity of 6a appears not to be derived from the kinetic resolution of the mono-brominated compound 6a.

Example 5—Theoretical Studies

Figure 7A:
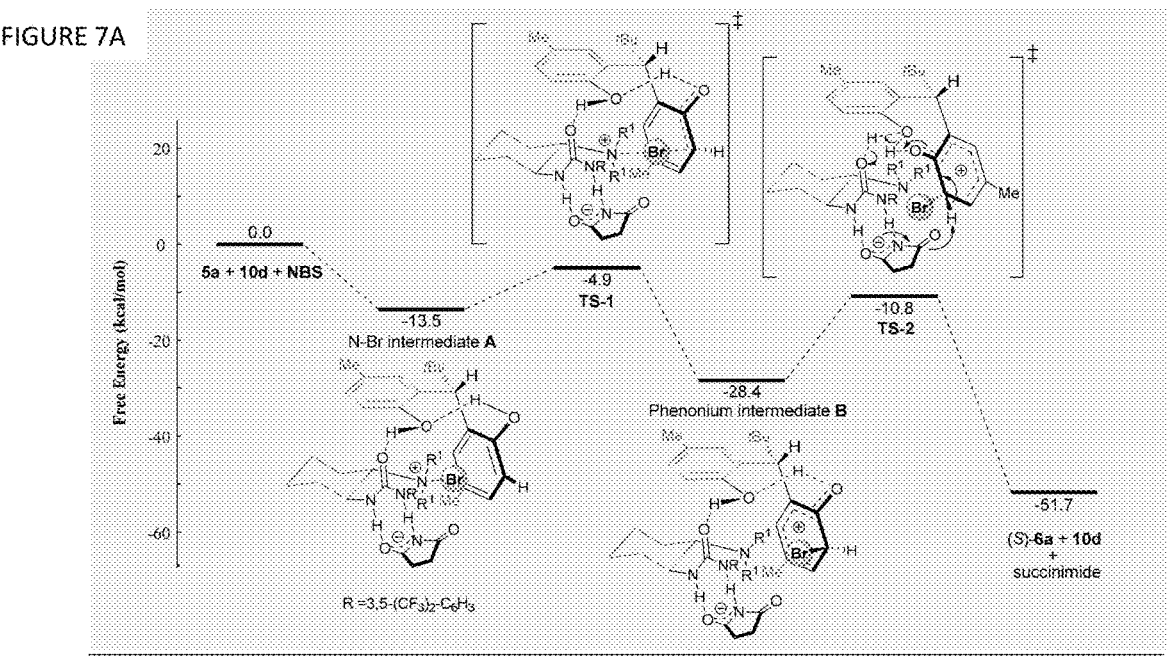
FIGS. 7A-7B. DFT calculation on the desymmetrizing asymmetric ortho-halogenation.
Figure 7B:
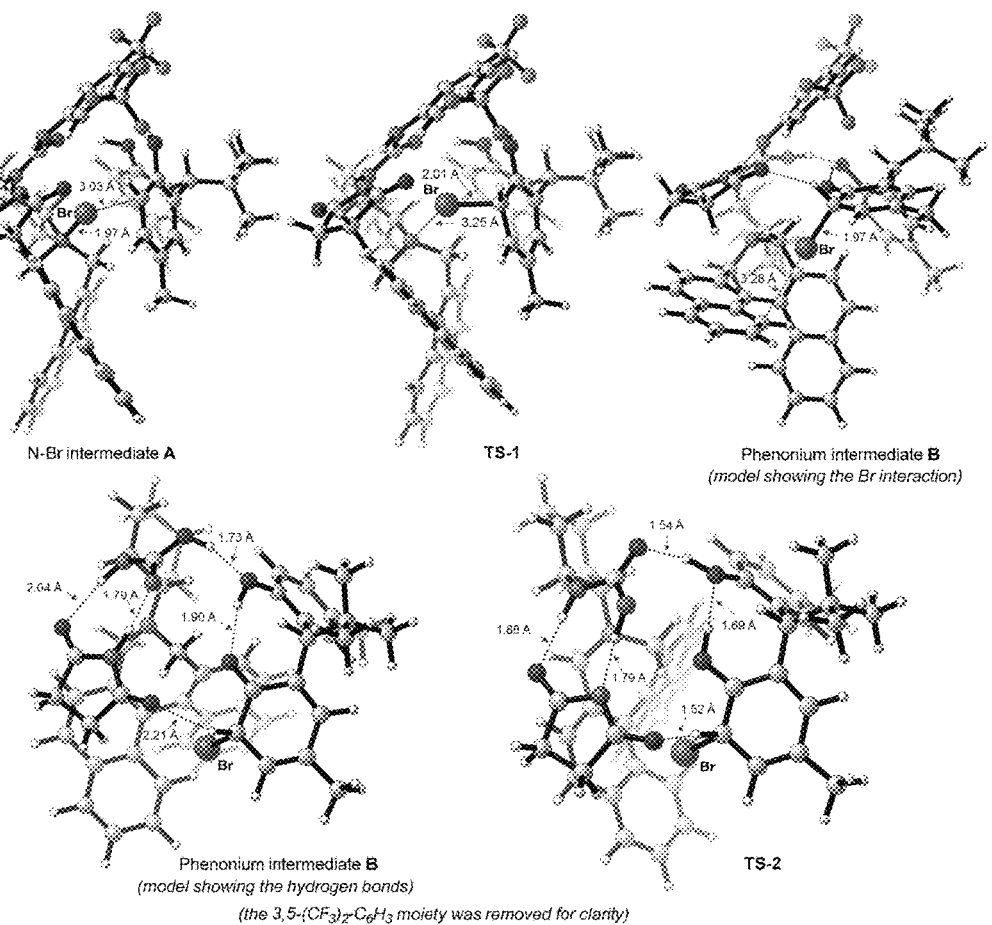

DFT calculations on the reaction with substrate 5a, catalyst 9d and NBS were conducted to gain further insight into the catalytic cycle. Based on the results of kinetic studies ($0.2^{th}$ order on substrate 5, $0^{th}$ order on catalyst 9, $1^{st}$ order on NBS) and non-linear effect experiment (linear relationship), a single molecule of each of the reaction components was used in the calculation model. All DFT calculations were carried out using Gaussian 09 (ver. D.01)[72] at the level of M06-2X hybrid-exchange correlation functional[73] with Grimme D3 dispersion correction[74] and 6-311G(d,p) basis set. All of the thermodynamic properties were evaluated at 195 K. The study began with the two most commonly proposed activation models of NBS (FIG. 7A), which involve: Lewis basic nitrogen activation of Br (intermediate A in WAY-1); dihydrogen activation of NBS (intermediate A' in WAY-2).[70] In the calculated free energy profiles, WAY-1 and WAY-2 give the same phenonium intermediate B before the formation of product 6a. In the two pathways, when intermediates A and A' are equally populated, WAY-1 is the predominant reaction avenue towards product 6 because the rate-determining step of WAY-2 encounters a significantly higher energy barrier (A'→TS1', 29.5 kcal/mol). It is possible that WAY-2 becomes the predominant pathway when A' is significantly more populated than A, which will happen when the barrier associated with the formation of A is considerably higher than that of A'. However, this situation seems less likely because $^1$H NMR experiment suggests that formation of the N—Br species is favorable.

Towards the formation of the major (S)-enantiomer of 6a, the Lewis base activation pathway initially gives the N—Br intermediate A stabilized by −13.5 kcal/mol. Intermediate A features hydrogen bond interaction between: (1) phenol substrate 5a and the urea's oxygen; (2) the urea N—Hs and the succinimide anion. Based on the optimized geometry, the Br on the amine is attacked by the enantiotopic phenolic moiety to produce the phenonium cationic intermediate B through transition state TS-1. The theoretical studies reveal that the intramolecular hydrogen bond between the two phenols in 5 plays a crucial role in fixing the geometry during the enantio-determining step TS-1. The acidity of one of the protons in the intramolecular hydrogen bond in 5 is enhanced, potentially, through the Brønsted-acid-assisted-Brønsted-acid mechanism,[68-69] which can facilitate the interaction between 5a and the urea's oxygen of catalyst 9d. In addition, it was subsequent deprotonation of the proton at the phenonium cation B by the succinimide anion accompanied by internal proton transfer through transition state TS-2 gives the product (S)-6a. It is calculated that TS2 is the rate-determining step of WAY-1 which has an energy barrier of 17.6 kcal/mol.

A reaction pathway towards the minor (R)-enantiomer of 6a based on the Lewis basic nitrogen activation of Br was also calculated. It was found that the free energy profile of (R)-6a is similar to that in the formation of (S)-6a except the rate-determining step is 1.4 kcal/mol higher than the TS-2 in the formation of (S)-6a. At the experimental temperature 195 K, the lower barrier for (S)-6a is associated with a rate constant that is at least 40 times larger. This calculated enantioselectivity is in good agreement with the experimental value. While a more detailed study is needed to elucidate the complete mechanism, our proposed pathway provides a self-consistent mechanistic picture that is in good agreement with the experimental results.

REFERENCES

1. Comprehensive asymmetric catalysis, Eds. E. N. Jacobsen, A. Pfaltz, H. Yamamoto, Springer, Berlin, 1999.
2. Asymmetric organocatalysis, Ed. B. List, Springer, Berlin, 2009.
3. Asymmetric catalysis on industrial scale: challenges, approaches, and solutions, Eds. H. U. Blaser, H.-J. Federsel, Wiley-VCH, German, 2010.
4. New frontiers in asymmetric catalysis, Eds. K. Mikami, M. Lautens, Wiley, Chicester, UK, 2007.
5. Catalytic asymmetric synthesis, Ed. I. Ojima, Wiley, New Jersey, 2010.
6. Chiral drugs, Eds. G.-Q. Lin, Q.-D. You, J.-F. Cheng, Wiley, New Jersey, 2011.
7. Farina V., Reeves J. T., Senanayake C. H., Song, J. J. (2006). Asymmetric synthesis of active pharmaceutical ingredients. Chem. Rev. 106, 2734-2793.
8. Trost, B. M. (2004). Asymmetric catalysis: An enabling science. Proc. Natl. Acad. Sci. 101, 5348-5355.
9. List, B., Yang, J. W. (2006). The organic approach to asymmetric catalysis. Science 313, 1584-1586.
10. MacMillan, D. W. C. (2008). The advent and development of organocatalysis. Nature 455, 304-308.
11. Yoon, T. P., Jacobsen, E. N. (2003). Privileged chiral catalysts. Science 299, 1691-1693.
12. Privileged Chiral Ligands and Catalysts, Ed. Q.-L. Zhou, Wiley-VCH, Weinheim, Germany, 2011.
13. Chen, Y., Yekta, S., Yudin, A. K. (2003). Modified BINOL ligands in asymmetric catalysis. Chem. Rev. 103, 3155-3212.
14. Bringmann, G., Mortimer, A. J. P., Keller, P. A., Gresser, M. J., Garner, J., Breuning, M. (2005). Atroposelective synthesis of axially chiral biaryl compounds. Angew. Chem. Int. Ed. 44, 5384-5427.
15. Brunel, J. M. (2005). BINOL: A versatile chiral reagent. Chem. Rev. 105, 857-897.
16. Akiyama, T. (2007). Stronger Brønsted acids. Chem. Rev. 107, 5744-5758.
17. Terada, M. (2008). Binaphthol-derived phosphoric acid as a versatile catalyst for enantioselective carbon-carbon bond forming reactions. Chem. Commun. 4097-4112.
18. Rueping, M., Kuenkel, A., Atodiresei, I. (2011). Chiral Brønsted acids in enantioselective carbonyl activations—activation modes and applications. Chem. Soc. Rev. 40, 4539-4549.
19. Ćorić, I., List, B. (2012). Asymmetric spiroacetalization catalysed by confined Brønsted acids. Nature 483, 315-319.
20. Sun, Z., Winschel, G. A., Borovika, A., Nagorny, P. (2012). Chiral phosphoric acid-catalyzed enantioselective and diastereoselective spiroketalizations. J. Am. Chem. Soc. 134, 8074-8077.
21. Wang, Y.-B., Tan, B. (2018). Construction of axially chiral compounds via asymmetric organocatalysis. Acc. Chem. Res. 51, 534-547.
22. Seebach, D., Beck, A. K., Heckel, A. (2001). TADDOLs, their derivatives, and TADDOL analogues: versatile chiral auxiliaries. Angew. Chem. Int. Ed. 40, 92-138.
23. Pellissier, H. (2008). Use of TADDOLs and their derivatives in asymmetric synthesis. Tetrahedron 64, 10279-10317.
24. Fu, Y., Xie, J.-H., Hu, A.-G., Zhou, H., Wang, L.-X., Zhou, Q.-L. (2002). Novel monodentate spiro phosphorus ligands for rhodium-catalyzed hydrogenation reactions. Chem. Commun. 480-481.
25. Xie, J.-H., Zhou, Q.-L. (2008). Acc. Chem. Res. 41, 581-593.
26. Duan, H.-F., Xie, J.-H., Qiao, X.-C., Wang, L.-X., Zhou, Q.-L. (2008). Enantioselective rhodium-catalyzed addition of arylboronic acids to α☐ketoesters. Angew. Chem. Int. Ed. 47, 4351-4353.
27. Hou, G.-H., Xie, J.-H., Yan, P.-C., Zhou, Q.-L. (2009). Iridium-catalyzed asymmetric hydrogenation of cyclic enamines. J. Am. Chem. Soc. 131, 1366-1367.
28. Chung, Y. K., Fu, G. C. (2009). Phosphine-catalyzed enantioselective synthesis of oxygen heterocycles. Angew. Chem. Int. Ed. 48, 2225-2227.
29. Ding, K., Han, Z., Wang, Z. (2009). Spiro skeletons: a class of privileged structure for chiral ligand design. Chem. Asian J. 4, 32-41.
30. Dong, K., Wang, Z., Ding, K. (2012). Rh(I)-catalyzed enantioselective hydrogenation of α-substituted ethenylphosphonic acids. J. Am. Chem. Soc. 134, 12474-12477.
31. Wu, C., Yue, G., Nielsen, C. D.-T., Xu, K., Hirao, H., Zhou, J. S. (2016). Asymmetric conjugate addition of organoboron reagents to common enones using copper catalysts. J. Am. Chem. Soc. 138, 742-745.
32. Ćorić, I., Müller, S., List, B. (2010). Kinetic resolution of homoaldols via catalytic asymmetric transacetalization. J. Am. Chem. Soc. 132, 17370-17373.
33. Xu, F., Huang, D., Han, C., Shen, W., Lin, X., Wang, Y. (2010). SPINOL-derived phosphoric acids: synthesis and application in enantioselective Friedel-Crafts reaction of indoles with imines. J. Org. Chem. 75, 8677-8680.
34. Xu, B., Zhu, S.-F., Xie, X.-L., Shen, J.-J., Zhou, Q.-L. (2011). Asymmetric N—H insertion reaction cooperatively catalyzed by rhodium and chiral spiro phosphoric acids. Angew. Chem. Int. Ed. 50, 11483-11486.
35. Wang, G.-P., Chen, M.-Q., Zhu, S.-F., Zhou, Q.-L. (2017). Enantioselective Nazarov cyclization of indole enones cooperatively catalyzed by Lewis acids and chiral Brønsted acids. Chem. Sci. 8, 7197-7202.
36. Birman, V. B., Rheingold, A. L., Lam, K.-C. (1999). 1,1'-Spirobiindane-7,7'-diol: a novel, $C_2$-symmetric chiral ligand. Tetrahedron: Asymmetry 10, 125-131.
37. Zhang, J.-H., Liao, J., Cui, X., Yu, K.-B., Zhu, J., Deng, J.-G., Zhu, S.-F., Wang, L.-X., Zhou, Q.-L., Chung, W. L., Ye, T. (2002). Highly efficient and practical resolution of 1,1'-spirobiindane-7,7'-diol by inclusion crystallization with N-benzylcinchonidinium chloride. Tetrahedron: Asymmetry 13, 1363-1366.
38. Li, S., Zhang, J.-W., Li, X.-L., Cheng, D.-J., Tan, B. (2016). Phosphoric acid-catalyzed asymmetric synthesis of SPINOL derivatives. J. Am. Chem. Soc. 138, 16561-16566.
39. Zheng, Z., Cao, Y., Chong, Q., Han, Z., Ding, J., Luo, C., Wang, Z., Zhu, D., Zhou, Q.-L., Ding, K. (2018). Chiral cyclohexyl-fused spirobiindanes: practical synthesis, ligand development, and asymmetric catalysis. J. Am. Chem. Soc. 140, 10374-10381.
40. Wang, Y.-B., Yu, P., Zhou, Z.-P., Zhang, J., Wang, J., Luo, S.-H., Gu, Q.-S., Houk, K. N., Tan, B. (2019). Rational design, enantioselective synthesis and catalytic applications of axially chiral EBINOLs. Nat. Catal. 2, 504-513.
41. Fujisaki, S., Eguchi, H., Omura, A., Okamoto, A., Nishida, A. (1993). Halogenation using N-halogenocompounds. I. Effect of amines on ortho-bromination of phenols with NBS.
Bull. Chem. Soc. Jpn. 66, 1576-1579.
42. Gnaim, J. M., Sheldon, R. A. (1995). Highly regioselective ortho-chlorination of phenol with sulfuryl chloride in the presence of amines. Tetrahedron Lett. 36, 3893-3896.
43. Saper, N. I., Snider, B. B. (2014). 2,2,6,6-Tetramethylpiperidine-catalyzed, ortho-selective chlorination of phenols by sulfuryl chloride. J. Org. Chem. 79, 809-813.
44. Maddox, S. M., Dinh, A. N., Armenta, F., Um, J., Gustafson, J. L. (2016). The catalyst-controlled regiodivergent chlorination of phenols. Org. Lett. 18, 5476-5479.
45. Xiong, X., Yeung, Y.-Y. (2018). Ammonium Salt-Catalyzed Highly Practical Ortho-Selective Monohalogenation and Phenylselenation of Phenols: Scope and Applications. ACS Catal. 8, 4033-4043.
46. Mori, K., Ichikawa, Y., Kobayashi, M., Shibata, Y., Yamanaka, M., Akiyama, T. (2013). Enantioselective synthesis of multisubstituted biaryl skeleton by chiral phosphoric acid catalyzed desymmetrization/kinetic resolution sequence. J. Am. Chem. Soc. 135, 3964-3970.
47. Hurtley, A. E., Stone, E. A., Metrano, A. J., Miller, S. J. (2017). Desymmetrization of diarylmethylamido bis(phenols) through peptide-catalyzed bromination: enantiodivergence as a consequence of a 2 amu alteration at an achiral residue within the catalyst. J. Org. Chem. 82, 11326-11336.
48. Diener, M. E., Metrano, A. J., Kusano, S., Miller, S. J. (2015). Enantioselective synthesis of 3-arylquinazolin-4 (3H)-ones via peptide-catalyzed atroposelective bromination. J. Am. Chem. Soc. 137, 12369-12377.
49. Barrett, K. T., Miller, S. J. (2013). Enantioselective synthesis of atropisomeric benzamides through peptide-catalyzed bromination. J. Am. Chem. Soc. 135, 2963-2966.
50. Moree, W. J., Li, B.-F., Jovic, F., Coon, T., Yu, J., Gross, R. S., Tucci, F., Marinkovic, D., Zamani-Kord, S., Malany, S., Bradbury, M. J., Hernandez, L. M., O'Brien, Z., Wen, J., Wang, H., Hoare, S. R. J., Petroski, R. E., Sacaan, A., Madan, A., Crowe, P. D., Beaton, G. (2009). Characterization of novel selective $H_1$-antihistamines for clinical evaluation in the treatment of insomnia. J. Med. Chem. 52, 5307-5310.

51. Huang, Z., Ducharme, Y., Macdonald, D., Robichaud, A. (2001). The next generation of PDE4 inhibitors. Curr. Opin. Chem. Biol. 5, 432-438.

52. Cheltsov, A. V., Aoyagi, M., Aleshin, A., Yu, E. C.-W., Gilliland, T., Zhai, D., Bobkov, A. A., Reed, J. C., Liddington, R. C., Abagyan, R. (2010). Vaccinia virus virulence factor N1L is a novel promising target for antiviral therapeutic intervention. J. Med. Chem. 53, 3899-3906.

53. Messaoudi, S., Hamze, A., Provot, O., Tréguier, B., Rodrigo De Losada, J., Bignon, J., Liu, J.-M., Wdzieczak-Bakala, J., Thoret, S., Dubois, J., Brion, J.-D., Alami, M. (2011). Discovery of isoerianin analogues as promising anticancer agents. ChemMedChem 6, 488-497.

54. Mondal, S., Panda, G. (2014). Synthetic methodologies of achiral diarylmethanols, diaryl and triarylmethanes (TRAMs) and medicinal properties of diaryl and triarylmethanes—an overview. RSC Adv. 4, 28317-28358.

55. Paquin, J.-F., Defieber, C., Stephenson, C. R. J., Carreira, E. M. (2005). Asymmetric synthesis of 3,3-diarylpropanals with chiral diene-rhodium catalysts. J. Am. Chem. Soc. 127, 10850-10851.

56. Fessard, T. C., Andrews, S. P., Motoyoshi, H., Carreira, E. M. (2007) Enantioselective preparation of 1,1-diarylethanes: aldehydes as removable steering groups for asymmetric synthesis. Angew. Chem. Int. Ed. 46, 9331-9334.

57. Imao, D., Glasspoole, B. W., Laberge, V. S., Crudden, C. M. (2009). Cross coupling reactions of chiral secondary organoboronic esters with retention of configuration. J. Am. Chem. Soc. 131, 5024-5025.

58. Tolstoy, P., Engman, M., Paptchikhine, A., Bergquist, J., Church, T. L., Leung, A. W.-M., Andersson, P. G. (2009). Iridium-catalyzed asymmetric hydrogenation yielding chiral diarylmethines with weakly coordinating or non-coordinating substituents. J. Am. Chem. Soc. 131, 8855-8860.

59. Woodmansee, D. H., Pfaltz, A. (2011). Asymmetric hydrogenation of alkenes lacking coordinating groups. Chem. Commun. 47, 7912-7916.

60. Taylor, B. L. H., Swift, E. C., Waetzig, J. D., Jarvo, E. R. (2011). Stereospecific nickel-catalyzed cross-coupling reactions of alkyl ethers: enantioselective synthesis of diarylethanes. J. Am. Chem. Soc. 133, 389-391.

61. Luan, Y., Schaus, S. E. (2012). Enantioselective addition of boronates to o-quinone methides catalyzed by chiral biphenols. J. Am. Chem. Soc. 134, 19965-19968.

62. Do, H.-Q., Chandrashekar, E. R. R., Fu, G. C. (2013). Nickel/bis(oxazoline)-catalyzed asymmetric negishi arylations of racemic secondary benzylic electrophiles to generate enantioenriched 1,1-diarylalkanes. J. Am. Chem. Soc. 135, 16288-16291.

63. Zhou, Q., Srinivas, H. D., Dasgupta, S., Watson, M. P. (2013). Nickel-catalyzed cross-couplings of benzylic pivalates with arylboroxines: stereospecific formation of diarylalkanes and triarylmethanes. J. Am. Chem. Soc. 135, 3307-3310.

64. Yonova, I. M., Johnson, A. G., Osborne, C. A., Moore, C. E., Morrissette, N. S., Jarvo, E. R. (2014). Stereospecific nickel-catalyzed cross-coupling reactions of alkyl Grignard reagents and identification of selective anti-breast cancer agents. Angew. Chem. Int. Ed. 53, 2422-2427.

65. Wang, Z., Ai, F., Wang, Z., Zhao, W., Zhu, G., Lin, Z., Sun, J. (2015). Catalytic enantioselective intermolecular desymmetrization of azetidines. J. Am. Chem. Soc. 137, 383-389.

66. Friis, S. D., Pirnot, M. T., Buchwald, S. L. (2016). Asymmetric hydroarylation of vinylarenes using a synergistic combination of CuH and Pd catalysis. J. Am. Chem. Soc. 138, 8372-8375.

67. Konev, M. O., Hanna, L. E., Jarvo, E. R. (2016). Intra- and intermolecular nickel-catalyzed reductive cross-electrophile coupling reactions of benzylic esters with aryl halides. Angew. Chem. Int. Ed. 55, 6730-6733.

68. Huang, Y., Unni, A. K., Thadani, A. N., Rawal, V. H. (2003) Hydrogen bonding: single enantiomers from a chiral-alcohol catalyst. Nature 424, 146.

69. Hirashima, S., Yamamoto, H. (2013). Development of new chiral Brønsted acid catalysis. J. Synth. Org. Chem. Jpn. 71, 1116-1125.

70. Lewis Base Catalysis in Organic Synthesis (Eds.: E. Vedejs, S. E. Denmark), Wiley-VCH, Weinheim, 2016.

71. Storer, R. I., Aciro, C., Jones, L. H. (2011). Squaramides: physical properties, synthesis and applications. Chem. Soc. Rev. 40, 2330-2346.

72. Frisch, M. J., Trucks, G. W., Schlegel, H. B., Scuseria, G. E., Robb, M. A., Cheeseman, J. R., Scalmani, G., Barone, V., Petersson, G. A., Nakatsuji, H. et al. Gaussian 09 Revision D. 01. Gaussian Inc. Wallingford CT (2009).

73. Zhao, Y., Truhlar, D. G. (2008). The M06 suite of density functionals for main group thermochemistry, thermochemical kinetics, noncovalent interactions, excited states, and transition elements: two new functionals and systematic testing of four M06-class functionals and 12 other functionals. Theor. Chem. Acc. 120, 215-241.

74. Grimme, S., Ehrlich, S., Goerigk, L. (2011). Effect of the damping function in dispersion corrected density functional theory. J. Comput. Chem. 32, 1456-1465.

We claim:

1. A method of halogenation, the method comprising contacting a reactant bisphenol with a source of a halogen in the presence of a catalyst under process conditions sufficient to prepare a halogenated bisphenol, wherein the halogen source is bromine, N-bromosuccinimide (NBS), N-bromophthalimide (NBP), N-bromoacetamide (NBA), 1,3-dibromo-5,5-dimethylhydantoin (DBDMH), 1,3-di bromo-5,5-diphenylhydantoin (DBDMH), 2,4,4,6-tetrabromo-2,5-cyclohexadienone (TBCO), chlorine, N-chlorosuccinimide (NCS), N-chlorophthalimide (NCP), 1,3-dichloro-5,5-dimethylhydantoin (DCDMH), 1,3-di chloro-5,5-diphenylhydantoin (DCDPH), 1-(4-methylbenzoyl)-3-chloro-5,5-diphenylhydantoin, iodine, or N-iodosuccinimide; and the catalyst is N-[3,5-bis(trifluoromethyl)phenyl]-N'-[(1S,2S)-2-(dimethylamino)cyclohexyl]urea; N-[3,5-bis(trifluoromethyl)phenyl]-N'-[(1S,2S)-2-(di-n-pentylamino)cyclohexyl]urea; 3-[[3,5-bis(trifluoromethyl) phenyl]amino]-4-[[(1S,2S)-2-(dimethylamino)cyclohexyl]amino]-3-cyclobutene-1,2-dione; N-[3,5-bis(trifluoromethyl)phenyl]-N'-[(1S,2S)-2-[(11bS)-3,5-dihydro-4H-dinaphth[2,1-c:1',2'-e]azepin-4-yl]cyclohexyl]urea; or N-[3,5-bis(trifluoromethyl)phenyl]-N'-[(1S,2S)-2-[(11bR)-3,5-dihydro-4H-dinaphth[2,1-c:1', 2'-e] azepin-4-yl]cyclohexyl]urea.

2. The method of claim 1, wherein the bisphenol is a mono-halogenated bisphenol and has alkyl, aryl, and/or electron-withdrawing substituents.

3. The method of claim 1, wherein the halogen source is a source of chlorine or a source of bromine.

4. The method of claim 3, wherein the chlorine source is DCDPH and the bromine source is NBS.

5. The method of claim 1, wherein the process conditions comprise the presence of a solvent; and, the process occurs at a temperature of about −80° C. to about 80° C., about −78° C. to about 0° C., or about −78° C. to about −40° C. for about 2 hours to about 7 days, about 1 day to about 5 days, or about 4 days to about 5 days.

6. The method of claim 5, wherein the solvent is an aromatic hydrocarbon, a carbon tetrachloride, or a combination thereof; and the ratio of aromatic hydrocarbon to carbon tetrachloride in the solvent is 2:1, 3:1, 4:1, or 5:1.

7. The method of claim 6, wherein the aromatic hydrocarbon is toluene.

8. The method of claim 5, wherein the process conditions further comprise the addition of a molecular sieve with a pore size of about 0.1 Å to about 100 Å, about 1 Å to about 10 Å, or about 4 Å.

9. The method of claim 1, further comprising cross-coupling the halogenated bisphenol to prepare a substituted bisphenol, wherein the halogen of the halogenated bisphenol is substituted with an acid.

10. The method of claim 9, wherein the acid is 1-naphthyl boronic acid and/or 2-naphthyl boronic acid.

11. The method of claim 9, further comprising preparing a dihydroxyl catalyst from the acid-substituted bisphenol.

12. The method of claim 11, wherein the dihydroxyl catalyst is a chiral phosphoric acid catalyst.

13. The method of claim 11, further comprising using the dihydroxyl catalyst to catalyze an asymmetric catalytic reaction.

14. The method claim 13, wherein the asymmetric catalytic reaction is an addition of an indole to an imine to prepare an adduct corresponding to the indole and the imine addition or a preparation of 3,4-dihydropyrimin-2(1H)-one using aldehyde, urea, and ethyl acetoacetate.

15. The method of claim 1, further comprising preparing a chiral phosphoramidite ligand from the halogenated bisphenol.

* * * * *